United States Patent [19]
Stefanchik et al.

[11] Patent Number: 5,951,574
[45] Date of Patent: Sep. 14, 1999

[54] MULTIPLE CLIP APPLIER HAVING A SPLIT FEEDING MECHANISM

[75] Inventors: David Stefanchik, Mason, Ohio; Rick D. Applegate, Florence, Ky.; Todd P. Omatis, Middletown, Ohio; William A. Burbank, Sandy Hook, Conn.; J. Renee Lupton, Belle Mead, N.J.

[73] Assignee: Ethicon Endo-Surgery, Inc., Cincinnati, Ohio

[21] Appl. No.: 09/178,389

[22] Filed: Oct. 23, 1998

[51] Int. Cl.$^6$ .................................................. A61B 17/04
[52] U.S. Cl. ........................... 606/143; 606/142; 227/901
[58] Field of Search ..................... 606/142, 143; 227/901

[56] References Cited

U.S. PATENT DOCUMENTS

| | | | |
|---|---|---|---|
| Re. 35,525 | 6/1997 | Stefanchik et al. | 606/142 |
| 4,325,376 | 4/1982 | Klieman et al. . | |
| 4,425,915 | 1/1984 | Ivanov . | |
| 4,427,008 | 1/1984 | Transue . | |
| 4,448,193 | 5/1984 | Ivanov . | |
| 4,450,839 | 5/1984 | Transue . | |
| 4,471,780 | 9/1984 | Menges et al. . | |
| 4,478,218 | 10/1984 | Mericle . | |
| 4,480,640 | 11/1984 | Becht . | |
| 4,522,207 | 6/1985 | Klieman et al. . | |
| 4,534,351 | 8/1985 | Rothfuss et al. . | |
| 4,549,544 | 10/1985 | Favaron . | |
| 4,565,199 | 1/1986 | Becht . | |
| 4,572,183 | 2/1986 | Juska . | |
| 4,598,711 | 7/1986 | Deniega . | |
| 4,611,595 | 9/1986 | Klieman et al. | 128/334 R |
| 5,030,226 | 7/1991 | Green et al. | 606/158 |
| 5,171,247 | 12/1992 | Hughett et al. | 606/142 |
| 5,171,249 | 12/1992 | Stefanchik et al. | 606/142 |
| 5,197,970 | 3/1993 | Green et al. | 606/158 |
| 5,431,668 | 7/1995 | Burbank, III et al. | 606/143 |
| 5,514,149 | 5/1996 | Green et al. | 606/158 |
| 5,700,270 | 12/1997 | Peyser et al. | 606/142 |

*Primary Examiner*—Gary Jackson
*Attorney, Agent, or Firm*—Matthew S. Goodwin

[57] ABSTRACT

A multiple clip applier includes a handle portion and a pair of handles pivotably connected to opposite sides of the housing. A shaft extends from the housing and has a plurality of clips located within. A pair of opposed moveable jaws are attached to and extend from the distal end of the shaft. The jaws receive one of the clips serially when they are open and form the clip received serially when they close. A moveable forming mechanism is operatively connected to the handles by a pair of forming links. As the handles close, the forming mechanism closes the jaws to form the clip received therein, and as the handles are opened, the forming mechanism opens the jaws to receive another clip therein. A feeding mechanism is provided that has a moveable feed plate attached to the handles by a pair of feed links. The feed plate is releasably coupled to a clip pusher. As the handles are closed, the clip pusher remains stationary and uncoupled with the moving feed plate. As the handles are opened, the clip pusher is operatively coupled to the feed plate and moves to place one of the clips into the jaws.

7 Claims, 17 Drawing Sheets

MULTIPLE CLIP APPLIER HAVING A SPLIT FEEDING MECHANISM

FIELD OF THE INVENTION

The present invention relates, in general, to surgical fastening devices and, more particularly, to multiple clip appliers.

BACKGROUND OF THE INVENTION

Clip appliers are quite well known in the surgical community and are used to ligate a blood vessel, a duct, or a portion of body tissue during surgery. Clip appliers have a pair of movable opposed jaws for holding and forming a ligation clip therebetween. The vessel is ligated or occluded when the ligating clip is crushed or formed on the vessel by the closing of the jaws. After clip formation, the jaws are opened, and the instrument must be reloaded for the next ligation. Initially, clip appliers required the manual reloading of a clip every time the instrument was fired.

The manual reloading process was time consuming and bothersome to surgeons, and the need for a multiple clip applier having both a clip forming mechanism to form a clip, and a multiple clip feeding mechanism that would repeatably feed a clip into the open jaws was recognized. The combination of a feeding and a forming mechanism was revolutionary and numerous examples of these multiple clip appliers exist in today's market. One such applier is the Ligaclip™ MCM30 multiple clip applier from Ethicon Endo-Surgery, Cincinnati, Ohio.

Of the multiple clip appliers that exist in today's market, there is a type of clip applier that may be considered as "automatic". The automatic clip applier is characterized as having a clip pusher and a jaw closure cam tube that move in opposite directions as the instrument is fired. Such a device was described by Deniega in U.S. Pat. No. 4,598,771 wherein a clip feeding mechanism moves proximally and a clip forming mechanism moves distally to close the clip located between the jaws. Once the clip is formed, the motions are reversed to load a new clip within the jaws. Additional multiple clip appliers are described in Green et al. U.S. Pat. Nos. 5,030,226 and 5,197,970, Stefanchik et al. U.S. Pat. No. 5,171,249, Hughett et al. U.S. Pat. No. 5,171,247, Burbank et al. U.S. Pat. Nos. 5,431,668, and Reissue No. Re. 35,525 by Stefanchik et al..

A Green et al. U.S. Pat. No. 5,541,149 describes the use of a pair of handles that are attached to the feeding and forming mechanism by a series of links in a similar manner to that taught by Burbank et al. The feeding mechanism has a clip pusher for pushing a clip into the open jaws and the forming mechanism has a camming member for closing the jaws upon the clip. The Green et al. '149 patent teaches when the handles are closed, the clip pusher moves proximally to pick up a clip and the camming member moves distally to close the jaws. As the handles are released, the camming member moves proximally to open the jaws, and the clip pusher moves distally to feed a clip in the jaws. Once the clip is fed into the jaws, the clip pusher remains in the distal most position (behind the jaws).

In many of the prior art multiple clip appliers, the positioning of the clip pusher at the distal most position is done to hold the jaws in the open position to prevent accidental closure of the jaws and to prevent proximal migration of the clip when exposed to tissue loads. In such appliers, the feeding and forming mechanisms require precise timing and coordinated movement of components to operate. For example, as the handles are initially closed, the clip pusher must first be retracted out of the jaw area or the jaws will collide with the clip pusher as they close.

This need for precise timing and control has resulted in the need for complex mechanical designs in many of the prior art clip appliers. The complexities of the components and the requirements for precision has increased the cost of the clip appliers. What is needed is a method of eliminating the requirement for precisely timed simultaneous motion of the feeding and the forming mechanisms as the handles are closed. This would reduce the precision of the components, eliminate the potential crushing of the clip pusher, and reduce costs.

It is an object of the present invention to eliminate the need for simultaneous opposed motion of the clip pusher with the forming system as the handles are closed. It is an additional object of the present invention to have the clip pusher place a clip into the open jaws of the instrument as the jaws open, and to retract the clip pusher into the shaft of the instrument when the handles are fully open. These actions eliminate the timing issues associated with clip appliers that require simultaneous motion of the clip pusher and the forming mechanism as the handles are closed.

Presently, there is no known multiple clip applier that can provide the surgeon with the improvements and benefits described above.

SUMMARY OF THE INVENTION

The present invention is a multiple clip applier having a handle portion and a pair of handles that are pivotally connected to the handle portion. A shaft extends from the handle portion and has a plurality of clips located therein.

A pair of opposed, moveable jaws are attached to and extend from the shaft. The jaws receive each of the clips serially when the jaws are in an open position and form each of the clips received serially when the jaws are moved to a closed position.

A moveable forming mechanism is operatively coupled to the handles by a pair of former links. The forming mechanism moving the jaws from the open position to the closed position as the handles are closed to form each of said clips received serially therein. The forming mechanism moving the jaws from the closed position to the open position as the handles are opened to receive each of the clips serially therein.

A feeding mechanism has a feed plate that is operatively coupled to the handles by a pair of feed links. The feed plate is moveable in response to the opening and closing of the handles. The feed plate is releasably operatively coupled to a clip pusher of the feeding mechanism. The clip pusher is stationary and uncoupled from the feed plate as the handles are closed. The clip pusher is moveable and operatively coupled with the feed plate as the handles are opened so as to place each of the clips serially from the shaft into the jaws.

In a preferred embodiment of the invention, the feed plate and the forming mechanism move in opposite directions as the handles are opened.

In an especially preferred embodiment of the invention, the clip pusher is operatively coupled to the feed plate by moving the proximal end of the clip pusher laterally to the axis of motion of the feed plate. This lateral movement operatively couples the clip pusher at an angle ($\theta$) with the feed plate. Further, after each clip is placed within the jaws by the clip pusher, the proximal end of the clip pusher moves laterally relative to the axis of motion of the feed plate to place the clip pusher parallel to the axis of motion. This action operatively uncouples the clip pusher from the feed plate.

A return spring couples the clip pusher to the handle portion and as the handles are opened, the clip pusher is decoupled from the feed plate, and the return spring moves the distal end of the clip pusher from a distal position adjacent to the clip placed within the jaws to a proximal position behind the distal most clip of the plurality of clips found within the shaft.

Significantly, the clip applier of the present invention eliminates the need for simultaneous motion of the clip pusher with the forming mechanism as the handles are closed. Consequently, a complex mechanical design similar to the prior art clip appliers is unnecessary, reducing component complexity and precision, as well as cost.

The clip applier of this invention can be used in any surgical or medical procedure where it is necessary or desired to occlude or ligate a vessel or tubular structure. For a better understanding of the invention and its unique features, reference is made to the accompanying drawings and descriptive matter in which the preferred invention is fully described.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
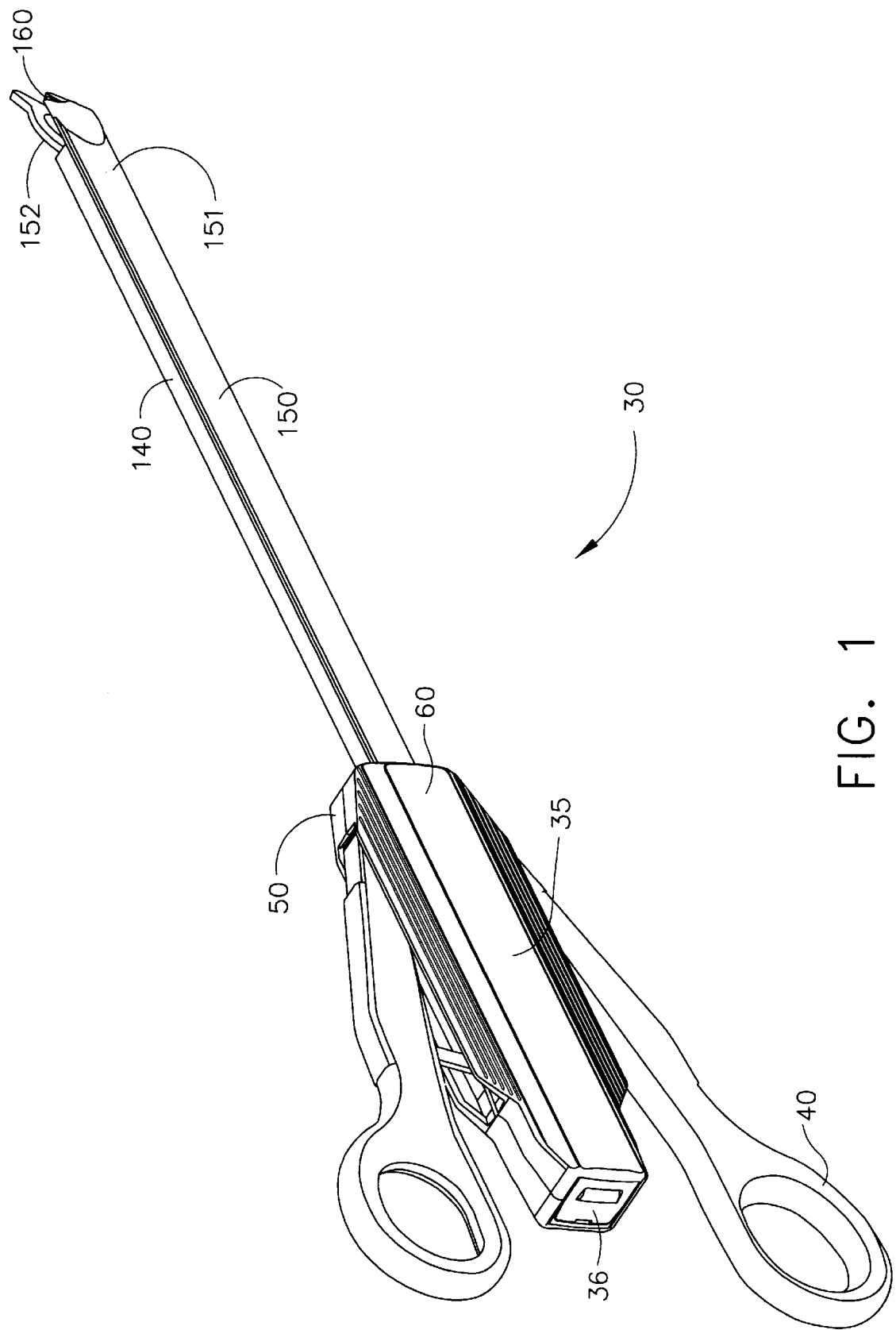
FIG. 1 is an isometric view of a surgical multiple clip applier of the present invention wherein the ring handles are in a fully open position.

The present invention is a multiple clip applier 30 for applying at least one surgical clip 160 (FIG. 1) to a human body. In particular, the present invention is a surgical clip applier having an improved feeding mechanism. The use of surgical clips 160 to ligate structures within the body such as vessels, ducts, and tissue is well known in the surgical art. The multiple clip applier 30 of the present invention is shown in FIG. 1 and has a distal pair of moveable jaws 152 for receiving clips serially therein when the jaws are open and forming the clip 160 received serially therein when the jaws are closed. The jaws 152 are rigidly connected to a handle portion 35 by a generally rectangular shaft 150. The shaft 150 has a structural "U" shaped outer wrap 140, a transparent upper shroud 151, and a clip magazine containing a plurality of clips (not shown) located therein. The handle portion 35 has a pair of symmetrical opposed ring handles 40 that are pivotably connected to the handle portion 35 and operatively connected to the moveable jaws 152 such that closure of the ring handles 40 results in the closure of the jaws 152 and the formation of each of the clips 160 received serially therein. Opening the ring handles 40 opens the jaws 152, releases the fully formed clip, and feeds an unformed clip 160 serially into the open jaws 152.

The multiple clip applier 30 of the present invention has a clip feeding mechanism, a clip forming mechanism, and the clip magazine similar to those described in Burbank et al. U.S. Pat. Nos. 5,431,668, Hughett et. al 5,171,247, Stefanchik et al., 5,171,249, and Re. 35,525 by Stefanchik et al., herein incorporated by reference. Like the Burbank et. al invention, the clip feeding mechanism and the clip forming mechanism of the preferred invention are operatively coupled to the moveable opposed ring handles 40 by a pair of feed links 42 (FIG. 3) and former links 41 (FIG. 3), respectively. Closure of the ring handles 40 results in opposite and simultaneous proximal and distal motion of the feeding and forming mechanisms.

The preferred invention is generally similar to the Burbank et al. invention but has a split or divided feeding mechanism. The feeding mechanism, hereafter referred to as feeding mechanism 100, 115 has two primary components; a feed plate 100 (FIG. 2) that moves simultaneously with the forming mechanism in the fashion of Burbank et al., Hughett et al., and Stefanchik et al., and a clip pusher 115 (FIG. 2) that remains generally stationary throughout most of the simultaneous motion. The clip pusher 115 is releasably coupled to the moving feed plate 100 (as the ring handles are opening) for the placement of a clip 160 into the opening jaws 152. The clip magazine supplies additional clips 160 to the feed mechanism 100, 115 for serial placement of the clips into the jaws 152 as described in the Burbank et al. and Stefanchik et al. patents.

Figure 2:
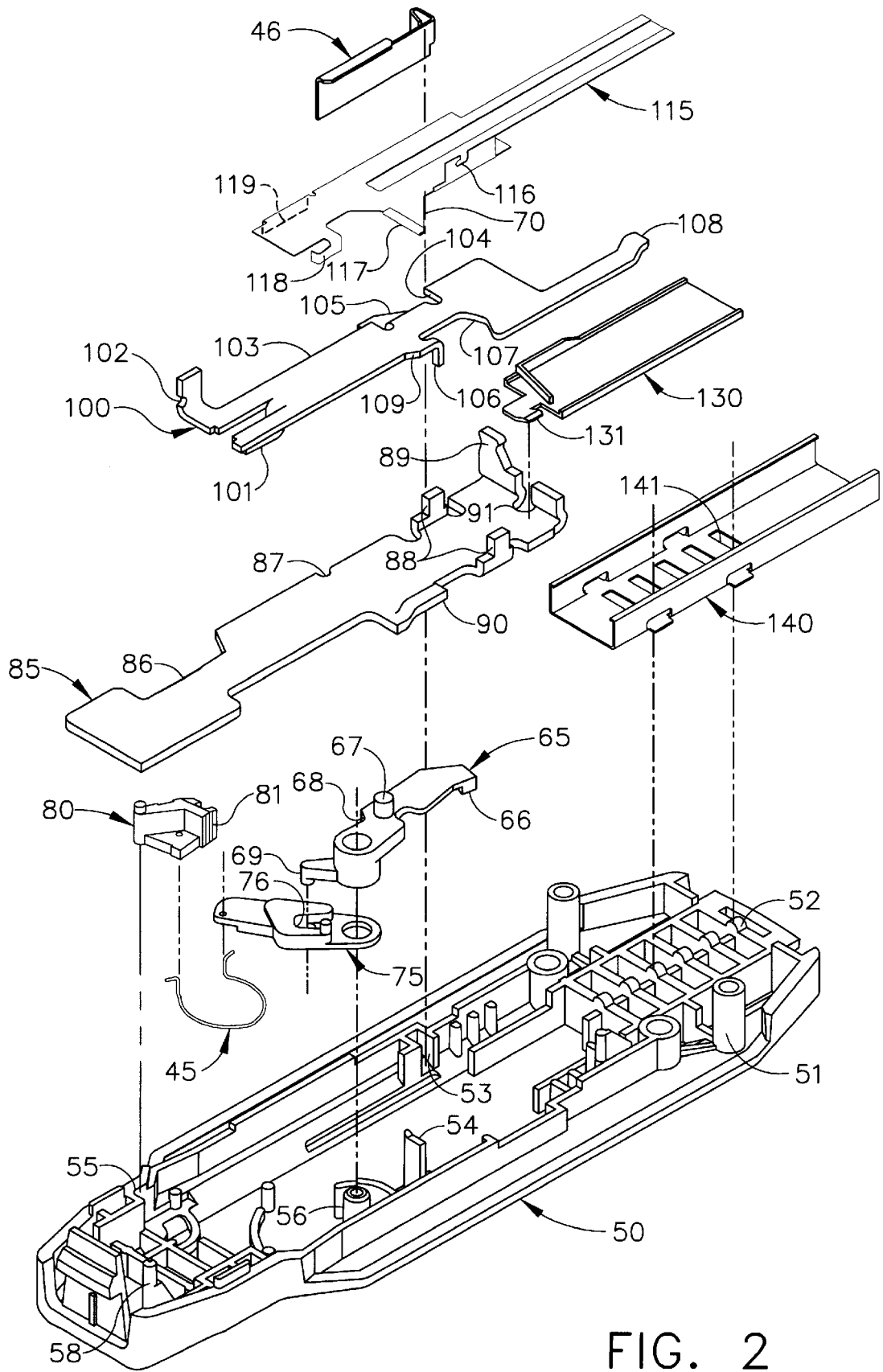
FIG. 2 is an exploded isometric view of the internal components of the handle portion of the multiple clip applier of FIG. 1.

FIG. 2 is an exploded view of the proximal end of the multiple clip applier 30 showing the internal components of the handle portion 35 and the shaft 150 (FIG.1). The ring handles 40, the former links 41, and feed links 42 are not show. The components of FIG. 2 are complex in shape and the reader is advised to return to FIG. 2 for identification or comprehension of features referenced below.

Figure 13:
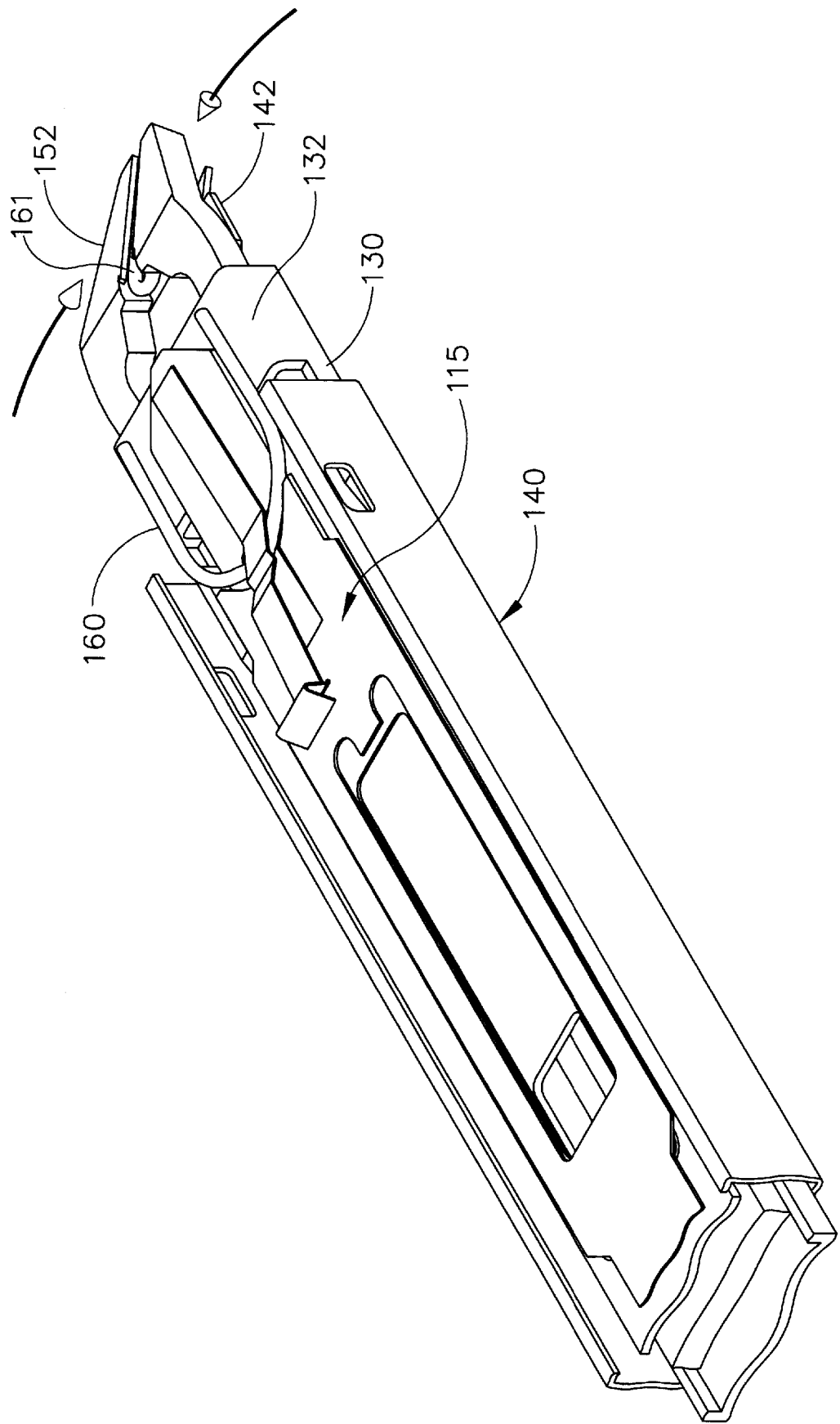
FIG. 13 is a partial isometric side elevational view of the distal end of the multiple clip applier wherein the jaws are fully closed and the top shroud and clip magazine are removed for clarity.

As described above, the split feeding mechanism of the present invention is formed from the assembly of two key components; the clip pusher 115 and the feed plate 100. The clip pusher 115 is a generally flat elongated member extending proximal to distal within the shaft 150, having a bifurcated distal end for pushing a clip 160 into the jaws 152 (FIG. 13). The proximal end of the clip pusher 115 widens within the handle portion 35 and slidably mounts on top of the feed plate 100. A locking tab 119 and a cantilever bias spring 118 extend downward adjacent to the distal end of the clip pusher 115 and straddle the proximal portion of the feed plate 100 distal to a feed spring tab 102. The interaction of these components in operatively coupling and decoupling the generally stationary clip pusher 115 with the moving feed plate 100 will be described in greater detail below. The feed plate 100 has a link hook 101 to engage the feed links 42 (not shown).

The forming mechanism of the present invention, hereafter referred to as forming mechanism (85, 130), has a pair of opposed jaws 152 that are moveable from an open to a closed position by a cam channel 130. The cam channel 130 is generally "U" shaped in cross section and extends from a channel hook 131 (FIG. 2) located within the handle portion 35 to a closure box 132 (FIG. 13) at the distal end of the shaft 150 for closing the jaws 152. The cam channel 130 is operatively coupled to a former plate 85 by placing the channel hook 131 into a channel notch 91. The former plate 85 has a pair of former posts 88 to operatively engage the former links 41.

The main structure of the present invention is formed from the assembly of the outer wrap 140 and a molded plastic base 50. The outer wrap 140 has at least one locking slot 141 that interlocks with a like number of locking blades 52 extending from the base 50 to attach the shaft 150 to the handle portion 35. The feeding mechanism (100, 115) and the forming mechanism (85, 130) described above slidably mount within the assembled base 50 and outer wrap 140. The ring handles 40 pivotably mount to a pair of handle posts 52 extending upwards from the base 50 (not shown).

The feeding mechanism 100, 115 and the forming mechanism 85, 130 of the present invention generally operate independently but are inter-operatively connected at certain key times by a trigger mechanism (henceforth referred to as trigger mechanism 65, 75 for controlling the timing and movement of the feeding mechanism (100, 115) relative to the forming mechanism 85, 130 in the fashion of the above cited Burbank, Hughett, and Stefanchik patents. The trigger mechanism 65, 75 is formed from the assembly of a trigger 65 and a trigger link 75 upon a trigger shaft 56 that extends upward from the base 50. A lock arm 69 of the trigger 65 engages a notch within the trigger link 75 to operatively couple the trigger 65 to the trigger link 75. The trigger mechanism 65, 75 rotates about the trigger shaft 56 in response to movement of the feed plate 100 as will be described later.

A semicircular C spring 45 operatively connects the trigger link 75 to a pawl 80 of an anti-backup mechanism (henceforth anti-backup mechanism 80, 86 that operatively engages the forming mechanism 85, 130 to prevent a partially formed loaded clip 161 (FIG. 10) from falling out of the jaws 152 should the surgeon release the ring handles 40 during jaw 152 closure. he anti-backup mechanism 80, 86 has a pawl 80 rotatably mounted within a pawl pocket 55 within the base 50 and has pawl teeth 81 for operatively engaging a toothed rack 86 upon the former plate 85. The trigger mechanism 65, 75, C spring 45, and pawl 80 form an over the center toggle such that a counterclockwise angular rotation of the trigger mechanism 65, 75 from a first to a second trigger position toggles the pawl teeth 81 of the anti-backup mechanism 80, 86 into engagement with the rack 86 of the former plate 85. This toggling motion engages the anti-backup mechanism 80, 86 and prevents proximal motion of the former plate 85. Application of a clockwise rotation to return the trigger mechanism 65, 75 to a first trigger position toggles the pawl 80 away from the former plate 85 and disengages the anti-backup mechanism 80, 86.

A lockout spring 46 mounts within the lockout receptacle 53 of the base 50 and locks the movement of the ring handles 40 when the last clip 160 is formed. The lockout spring 46 prevents movement of the ring handles 40 by engaging a notch 87 in the forming plate 85 preventing movement of the former plate 85.

Figure 3:
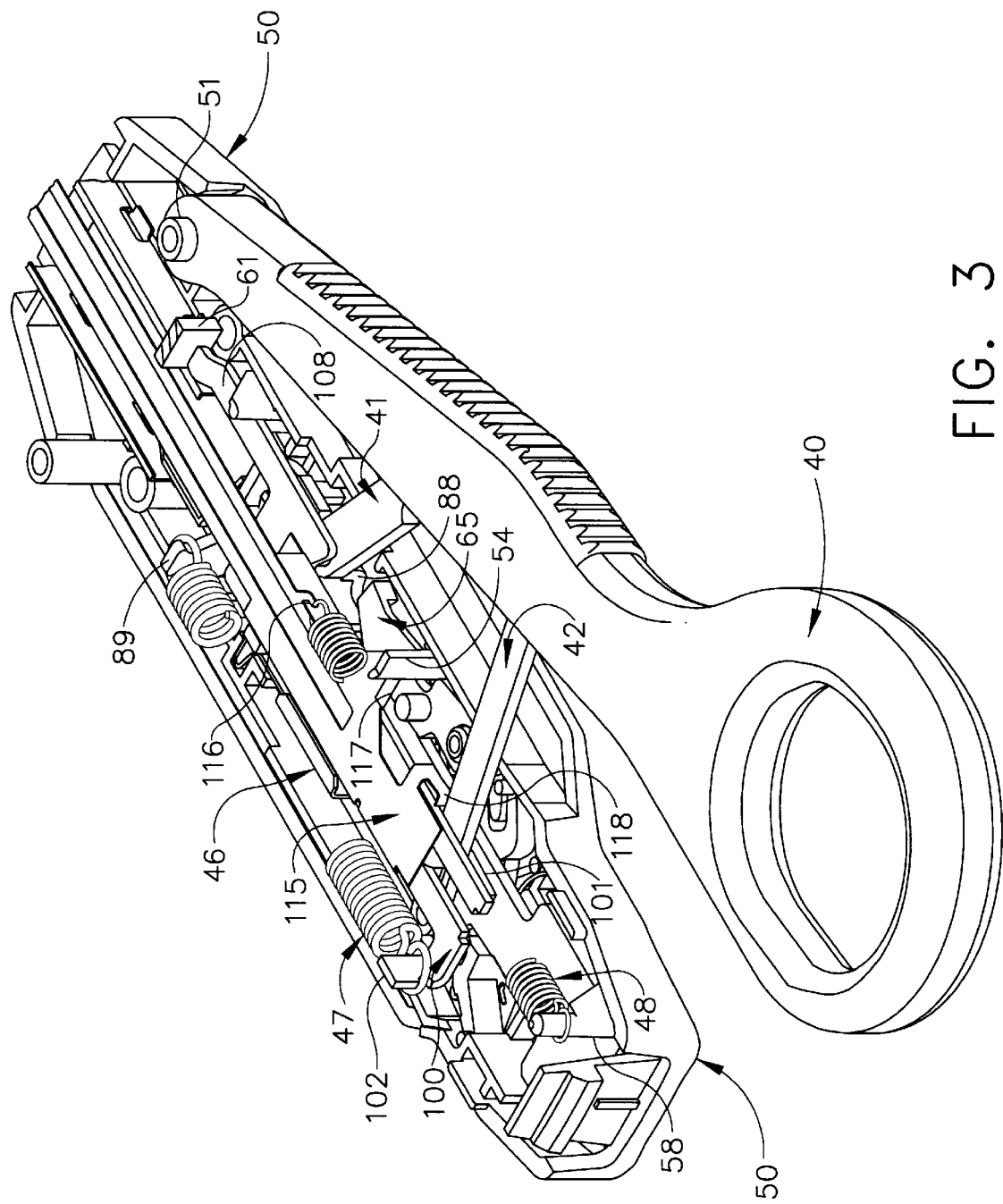
FIG. 3 is an isometric view of the assembled internal components of the handle portion of the multiple clip applier of FIG. 1 with the cover and one ring handle removed for clarity.

FIGS. 3–18 show the assembled multiple clip applier 30. In FIGS. 3, 8, and 11, one of the ring handles 40, feed links 42, and former links 41 are removed for clarity. In FIGS. 3, 4, 6, 8, 9, 11, 12, 13, and 16, the cover 60 is removed to show the internal components.

Figure 4:
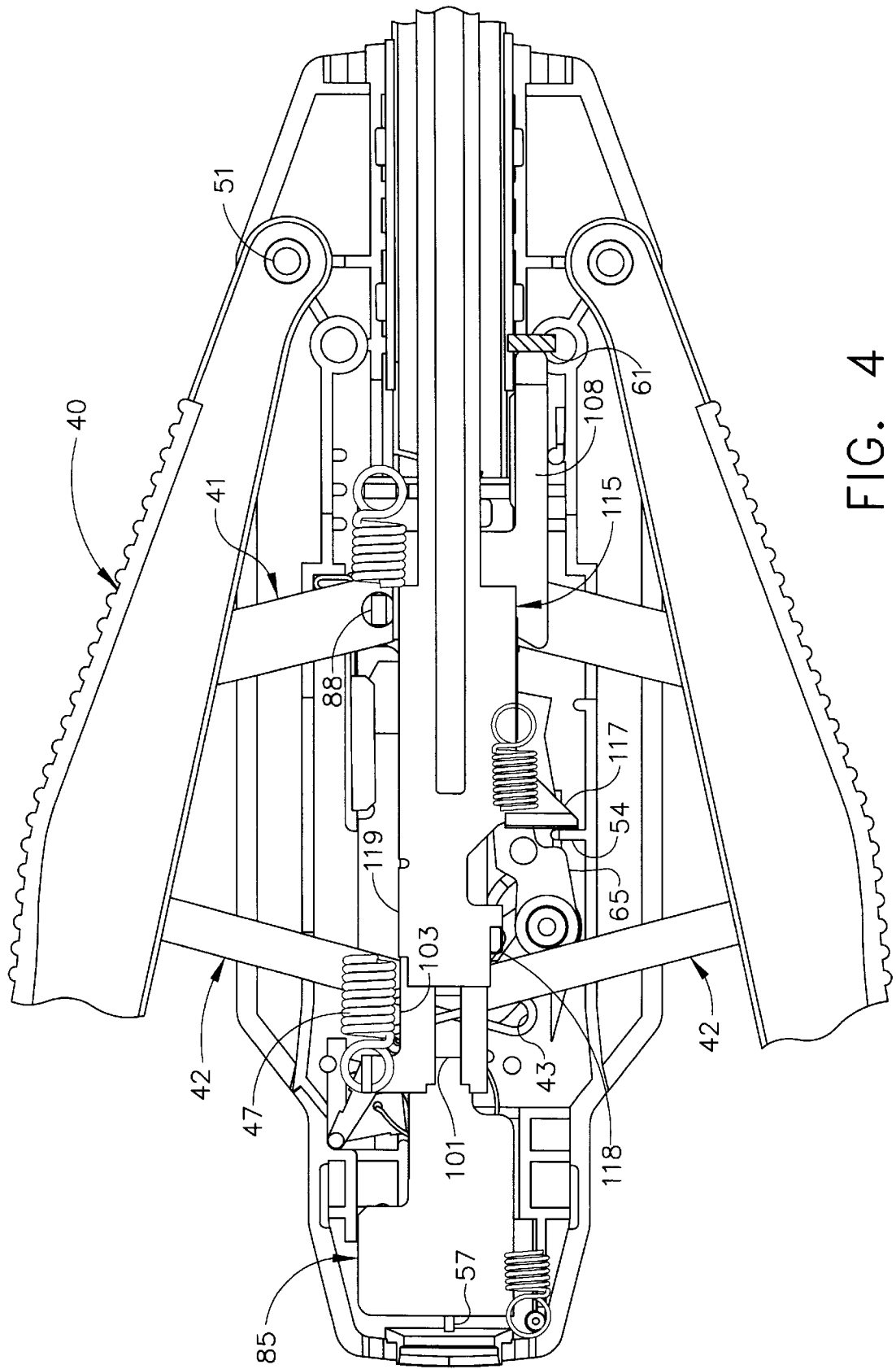
FIG. 4 is a top view of FIG. 3 wherein the ring handles are in a fully opened position.
Figure 5:
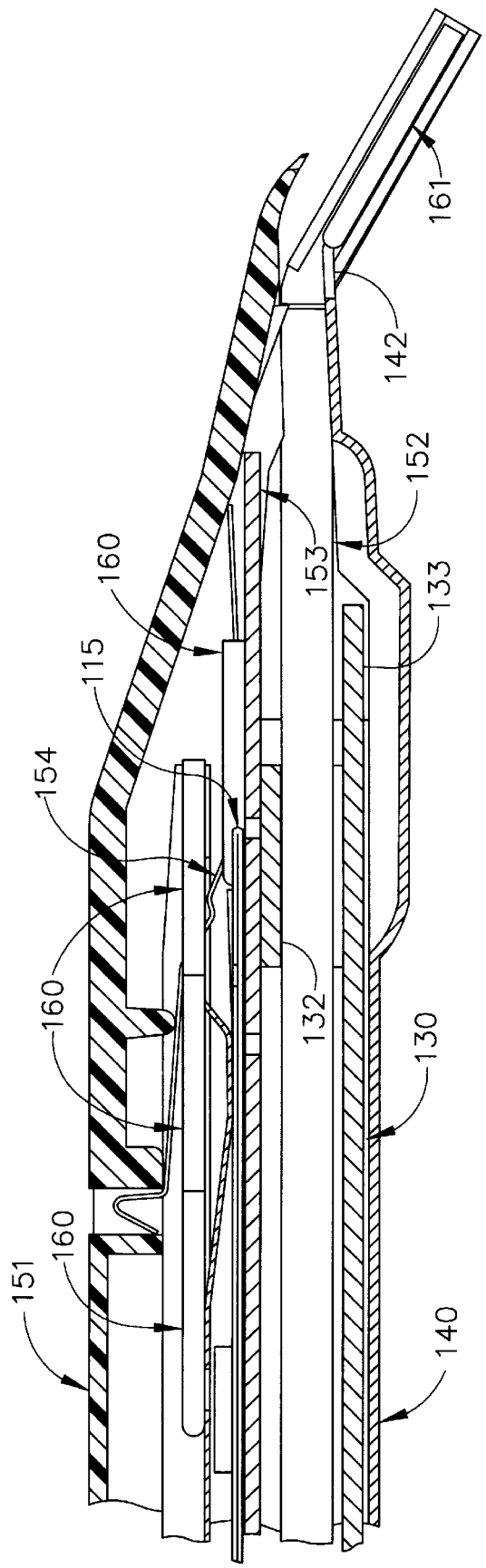
FIG. 5, is a bottom view, in cross section, of the distal end of the multiple clip applier of FIG. 1 showing an unformed clip loaded in the jaw.

Turning now to FIGS. 3, 4, and 5, the assembled instrument is shown ready for use wherein the loaded clip 161 is located within the open jaws 152 (FIG. 5) and the ring handles 40 are fully open (FIGS. 3 and 4). Within these views, the forming mechanism 85, 130 is shown in the in the proximal most position wherein the proximal end of the former plate 85 is against a former plate stop 57 of the base 50 and the feeding mechanism 100, 115 is in the distal most position wherein the stop arm 108 of the feed plate 100 is against a feed stop rib 61 of the cover 60. As best shown in FIG. 3 and 4, a firing spring 47 is shown attached to former spring tab 89 of the forming plate 85 and to the feed spring tab 102 of the feed plate 100. The firing spring 47 biases the forming mechanism 85, 130 in a proximal direction, the feed mechanism 100, 115 in a distal direction, and the ring handles 40 open.

FIGS. 3, 4, and 5 shows the feed mechanism 100, 115 of the present invention wherein the clip pusher 115 is disconnected, e.g. not operatively coupled to the feed plate 100. The locking tab 119 and the bias spring 118 of the clip pusher 115 are shown straddling the feed plate 100, as previously described. The locking tab 119 is in sliding contact with a tab surface 103 of the feed plate 100. A return spring 48 attaches to a spring notch 116 of the clip pusher 115 and a spring post 58 that extends upwards from the base 50. The return spring 48 biases the clip pusher 115 distally to place a pusher stop 117 of the clip pusher 115 against a pusher stop post 54 extending upwards from the base 50. It is important to note that the clip pusher 115 is stationary and uncoupled from the feed plate as the handles are closed as shown in FIGS. 3–12.

The forming mechanism 80, 85 of the present invention is shown in the distal most position wherein the anti-backup mechanism is activated. The pawl 80 is rotated into operative engagement with the rack 86 of the former plate 85.

FIG. 5 shows the distal end of the multiple clip applier 30. The loaded clip 161 is located within the fully open jaws 152. The loaded clip 161 is constrained from rearward motion by a flexible outer wrap tongue 142 (as best shown in FIG. 13) that extends between the jaws 152 from the outer wrap 140. The outer wrap tongue 142 also prevents closure of the jaws 152 by acting as a block that prevents inward motion of the jaws 152 and accidental forming of the loaded clip 161. The clip pusher 115 is in the proximal most position in contact with a partially fed clip 160 in the first staged position.

Figure 6:
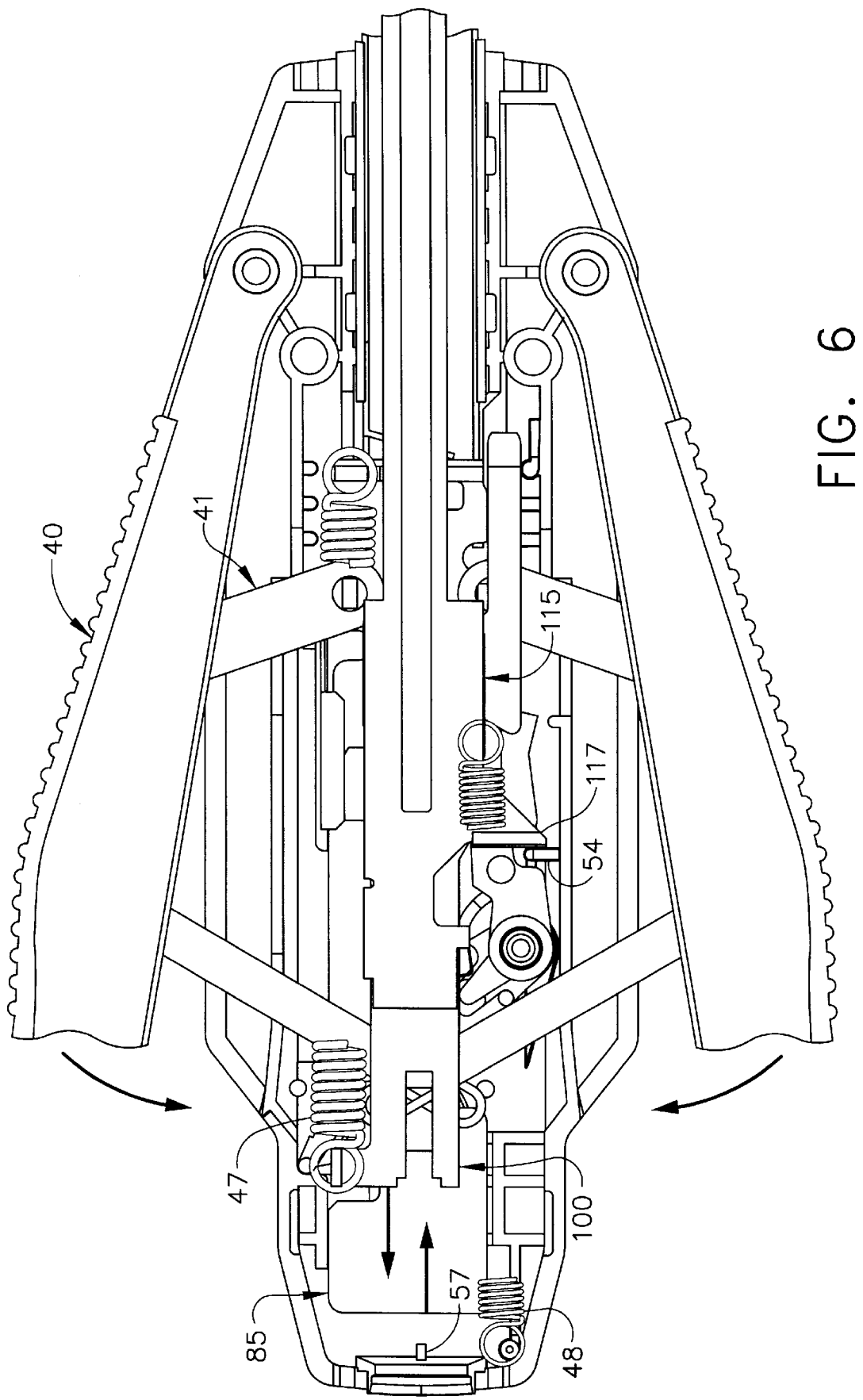
FIG. 6 is a top view of the handle portion of FIG. 4 wherein the ring handles are in a first partially closed position and the internal components are moved from the at rest positions of FIG. 4.
Figure 7:
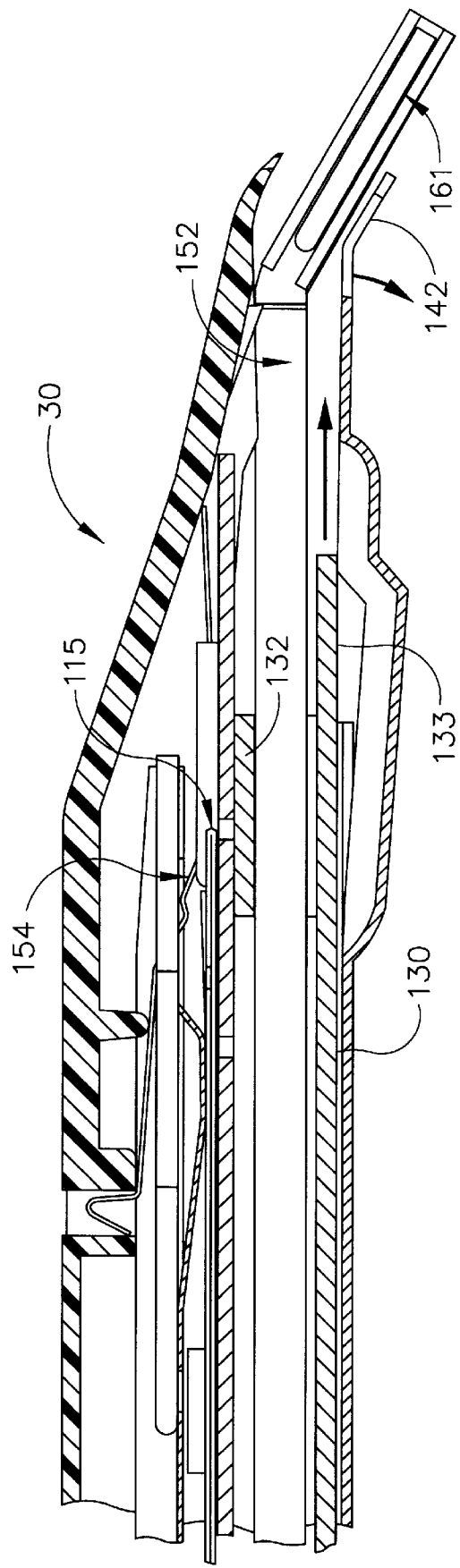
FIG. 7 is similar to the bottom view of the distal end of the instrument as shown in FIG. 5 showing the jaws are in a first partially closed position from the movement of the ring handles as shown in FIG. 6.
Figure 8:
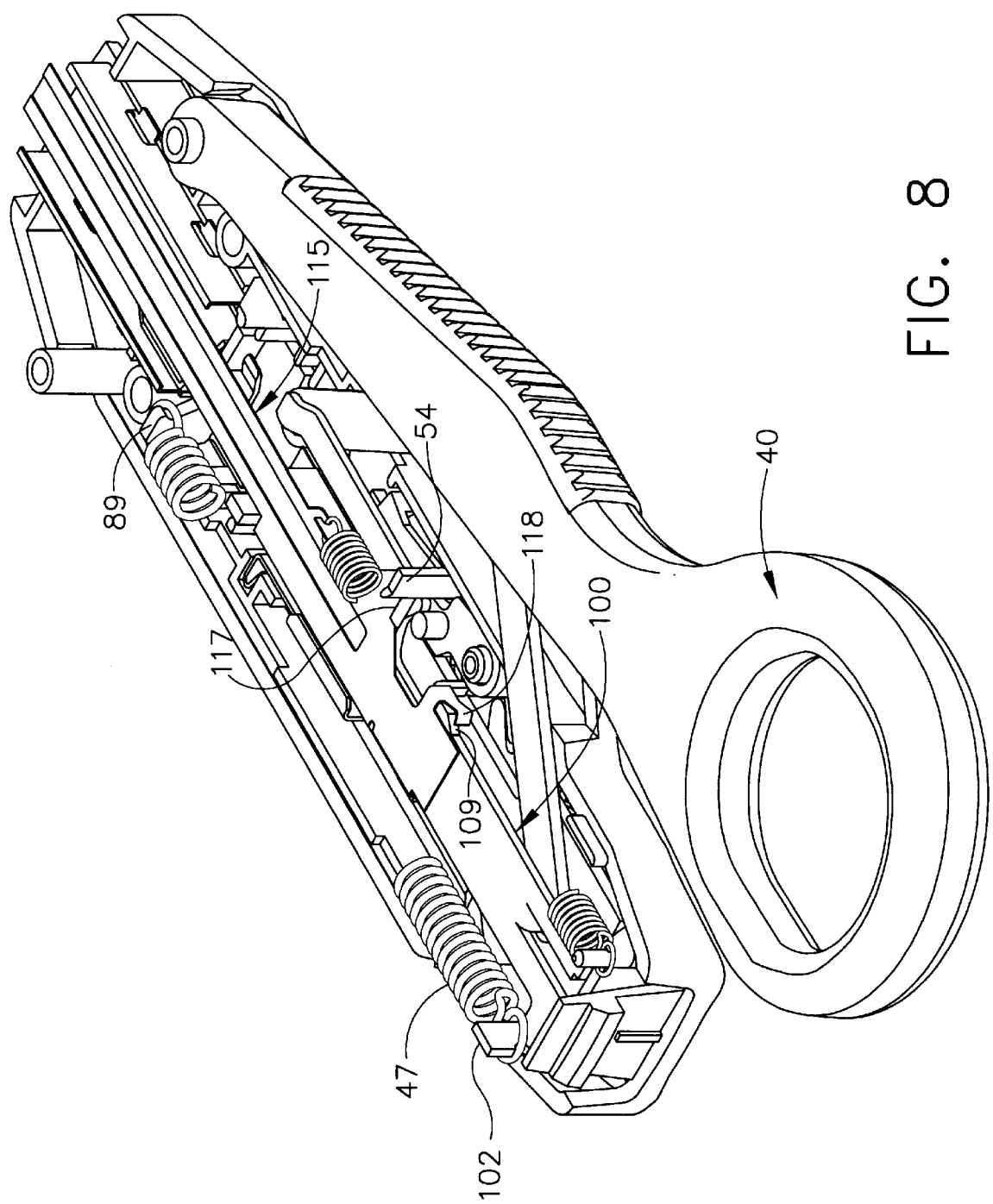
FIG. 8 is similar to the isometric view of the handle components of FIG. 3, but with the ring handles moved to a second partially closed position.

FIGS. 6 and 7 shows the multiple clip applier of the present invention wherein the ring handles 40 are moved to a first partially closed position and the loaded clip 161 is partially formed within the closing jaws 152. As best shown in FIG. 6, the former plate 85 is moving away from the former plate stop 57 in the distal direction, as indicated by the arrow located at the proximal end of the former plate 85. The feed plate 100 is moving in a proximal direction as indicated by the arrow located at the proximal end of the feed plate 100. Moving the feed plate 100 proximally and the former plate 85 distally lengthens the firing spring 47. As described above, the clip pusher 115 is stationary.

Turning now to the distal end of the instrument shown in FIG. 7, the cam channel 130 is shown moving distally within the shaft of the present invention to partially close the jaws 152 and the loaded clip 161. A cam tongue 133 extends distally from the closure box 132 (FIG. 13) of the cam channel 130. The outer wrap tongue 142 is deflected out of the closing jaws 152 by contact with the distally moving cam tongue 133.

Figure 9:
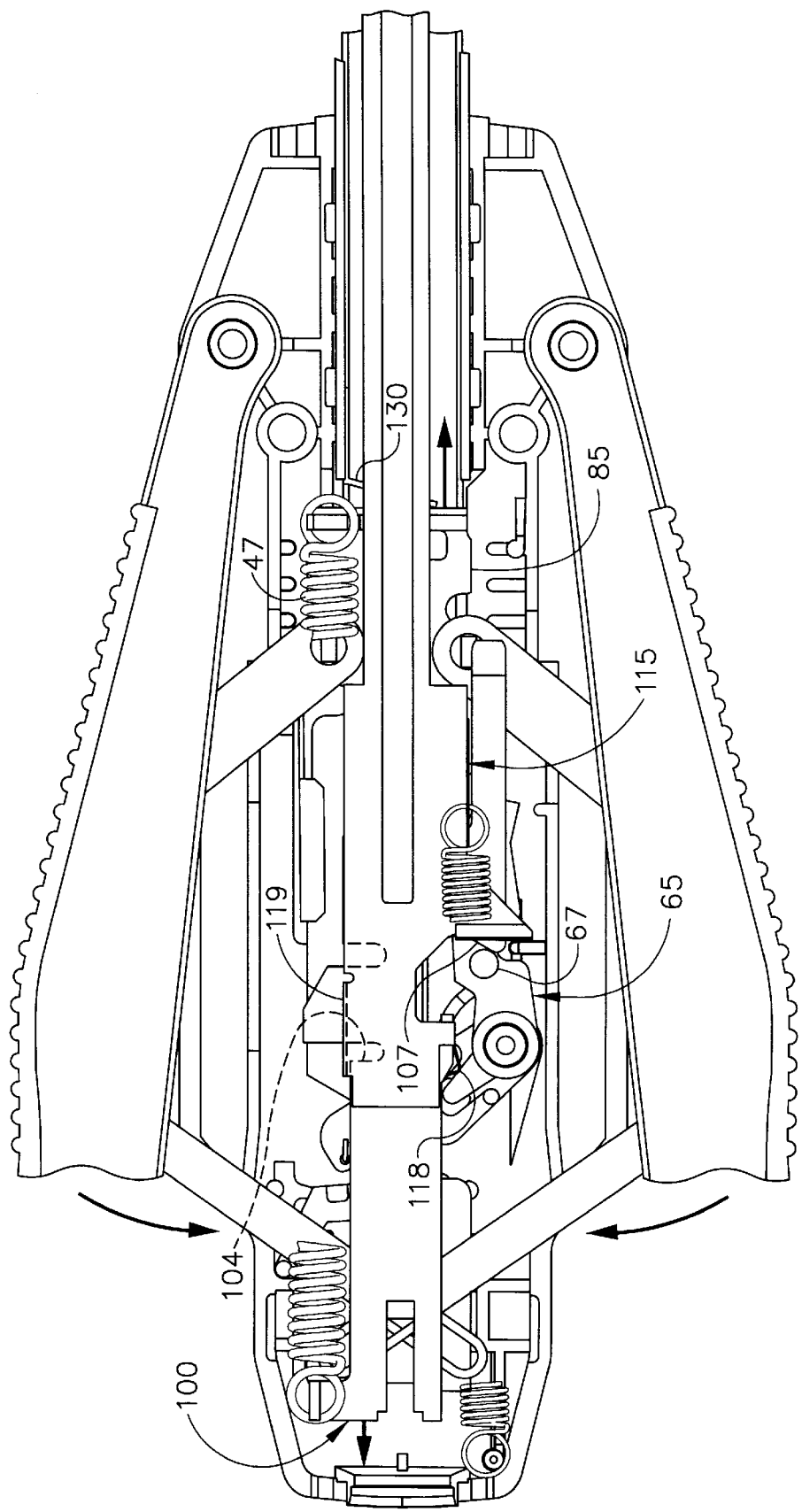
FIG. 9 is a top view of FIG. 8 wherein the ring handles are in a second partially closed position.
Figure 10:
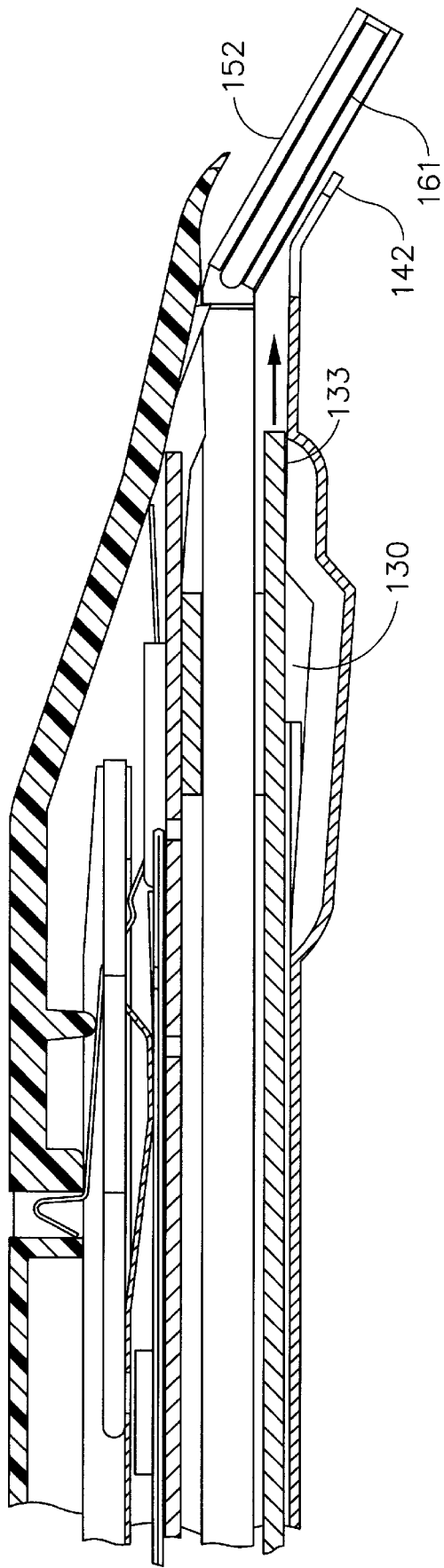
FIG. 10 is similar to that of FIG. 7, but with the jaws in a second partially closed position and the end effector components repositioned by the movement of the ring handles as shown in FIG. 9.
Figure 11:
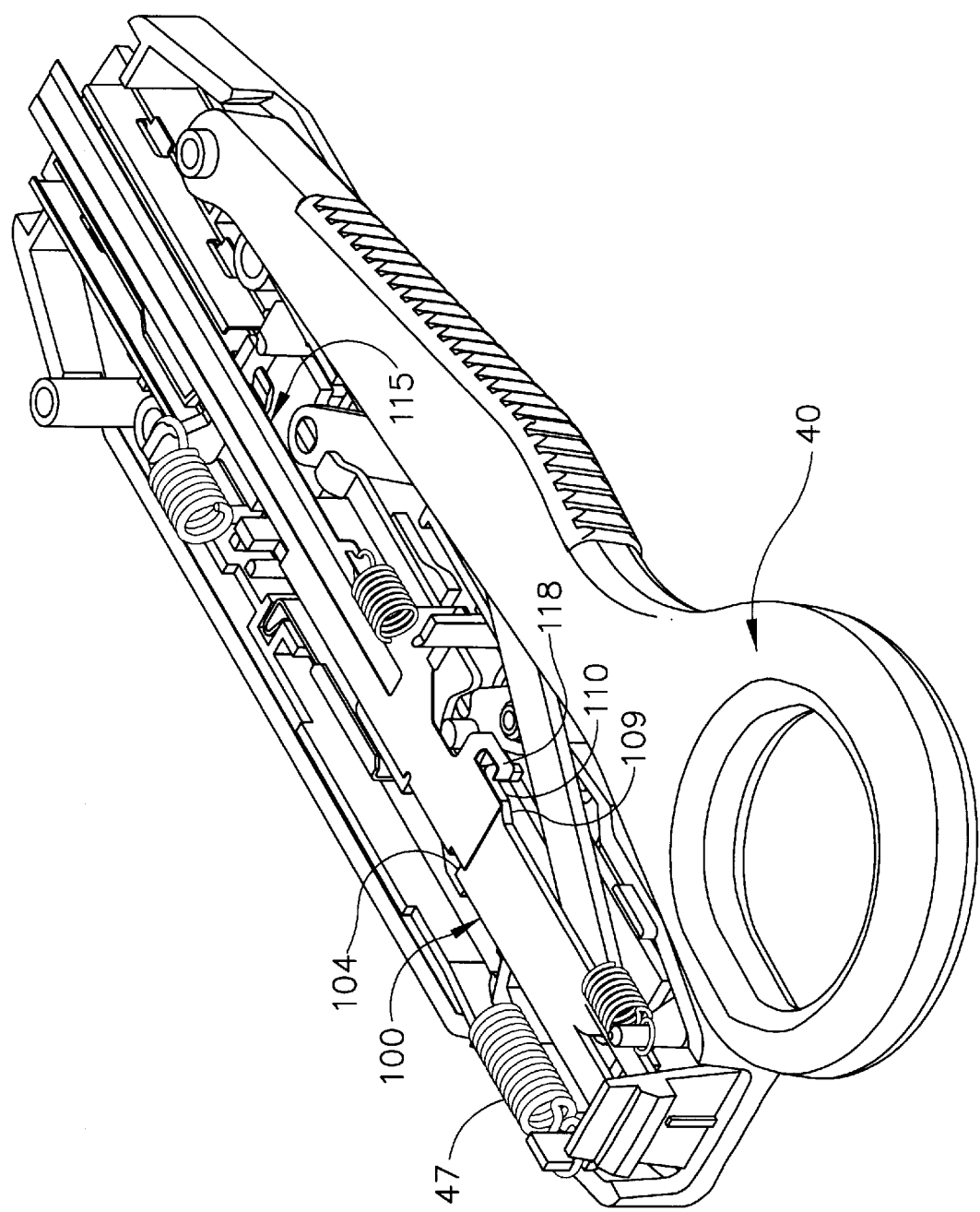
FIG. 11 is similar to the isometric view of the handle components of FIG. 8, but with the ring handles moved to a fully closed position.

FIGS. 8, 9, and 10 shows the ring handles 40 of the multiple clip applier 30 in a second partially closed position wherein the moving feed plate 100 of the feeding mechanism 100, 115 is beginning to engage coupling features of the stationary clip pusher 115 and the closing jaw 152 continues to form the loaded clip 161. In FIG. 9, arrows are shown at the proximal end of the feed plate 100 and at the distal end of the former plate 85 to indicate the direction of motion. The motion of the feed plate 100 and the forning plate 85 are continuing to lengthen the firing spring 47. The anti-backup mechanism 80, 86 is engaged with the forming mechanism 85, 130.

The view of FIGS. 8 and 9 shows the feeding mechanism 100, 115 shortly before the operative coupling of the stationary clip pusher 115 with the moving feed plate 100. The feed plate 100 is moving distally and the locking tab 119 of the clip pusher 115 is sliding against the tab surface 103 (FIG. 2) of the feed plate 100 adjacent to a locking notch 104 (dashed lines) located on the feed plate 100. The locking tab 119 is biased downwards (FIG. 9) against the moving tab surface 103 of the feed plate 100 by the deflection of the opposed cantilever bias spring 118 against a bias ramp 109 (as best shown in FIG. 8) on the feed plate 100. The locking notch 104 (as best shown in FIG. 2) is a receptacle for the capture of the locking tab 119.

The trigger mechanism 65, 75 has remained stationary during the closure cycle as shown in FIGS. 3, 4 and 6. In FIGS. 8 and 9, a trigger post 67 extending upwards from the trigger 65 is shown contacting the inner surface of a trigger cam notch 107 located within the distally moving feed plate 100. This contact is rotating the trigger mechanism 65, 75 in a counter-clockwise direction.

FIG. 10 shows the distal end of the multiple clip applier 30 prior to full closure of the jaws 152 upon the partially formed loaded clip 161. The horizontal arrow indicates the direction of travel of the cam channel 130.

Figure 12:
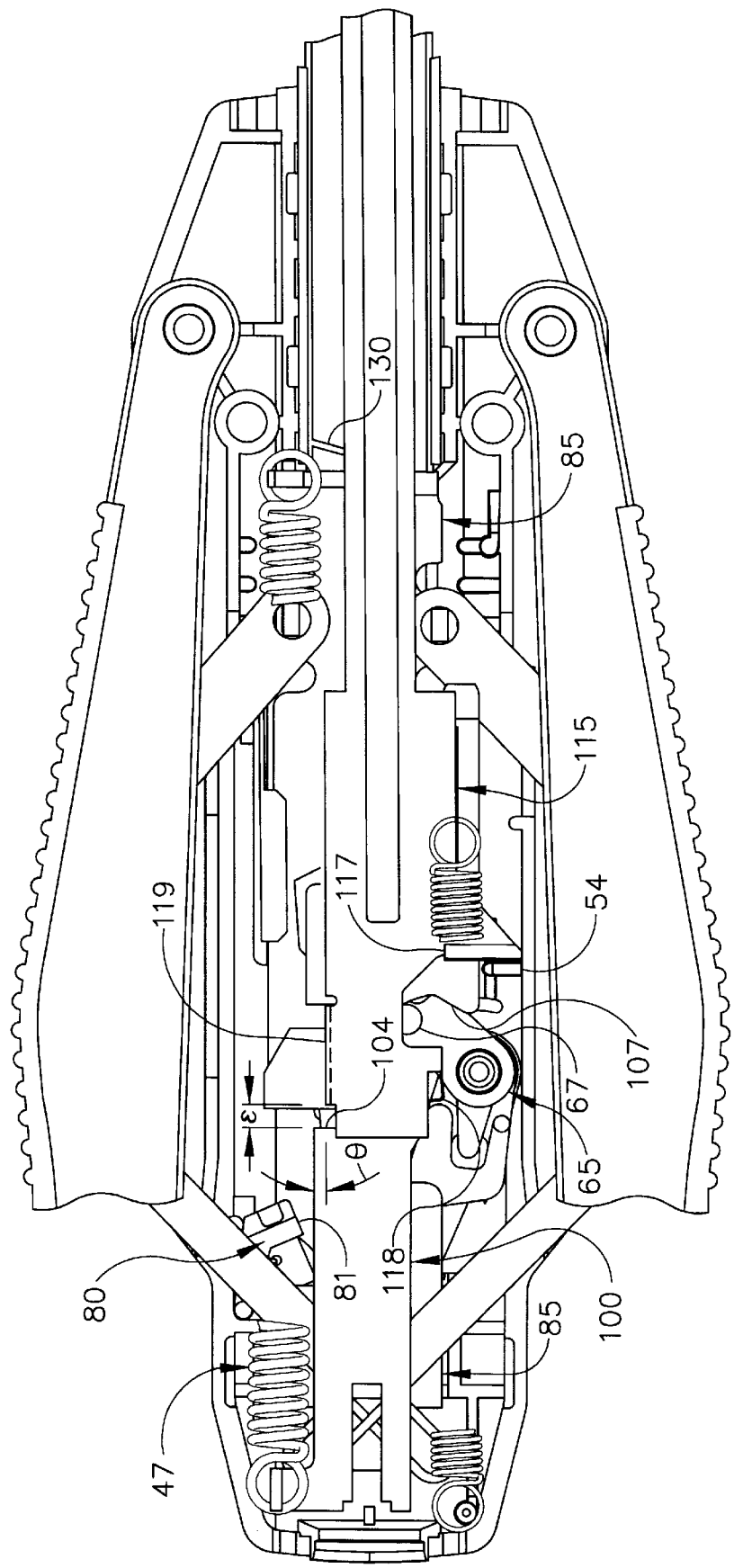
FIG. 12 is a top view of FIG. 11 wherein the ring handles are in a fully closed position.

FIGS. 11, 12 and 13 show the ring handles 40 in a fully closed position to fully form the loaded clip 161 within the jaws 152. In FIGS. 11 and 12, the feed plate 100 is stationary at the distal most position and the former plate 85 is stationary at the proximal most position. The firing spring 47 is shown at the maximum extension.

Turning now to the feeding mechanism 100, 115, the clip pusher 115 is shown engaged with, but not operatively coupled to the feed plate 100. The distal movement of the feed plate 100 has moved the tab surface 103 (FIG. 2) past the stationary locking tab 119 of the clip pusher 115 by an amount $\epsilon$. The locking tab 119 is biased downward into the locking notch 104 (FIG. 12) by the contact of the bias spring 118 with the bias dwell 110 on the feed plate 100. This motion is lateral to the axis of motion and has placed the clip pusher 115 at an angle $\theta$ with both the feed plate 100 and the longitudinal axis of the instrument. The laterally moved clip pusher 115 will be operatively coupled with the feed plate 100 as described below.

The trigger mechanism 65, 75 has been rotated to the second position as described above by the continued contact of the trigger post 67 within the trigger cam notch 107. The rotation of the trigger mechanism 65, 75 has activated the over-the-center toggle and disengaged the anti-backup mechanism 80, 86 by rotating the pawl 80 away from the rack 86 (FIG. 2) on the former plate 85. Additionally, the rotation of the trigger mechanism (65, 75) has placed a trigger notch 68 (FIG. 2) of the trigger 65 into longitudinal alignment with a trigger tab 106 (FIG. 2) of the feed plate 85 (not shown).

FIG. 13 shows an isometric view of the distal end of the multiple clip applier showing the jaws fully closed upon a fully formed loaded clip 161. The upper shroud 151 and a number of the clip magazine mechanism components are removed from this view for clarity. The cam channel 130 is in the distal most position and is forcing the jaws 152 together (see arrows) to fully form the loaded clip 161. A second clip 160 is shown in a first staged position wherein the clip 160 has been fed from the clip magazine mechanism and is positioned within the bifurcated end of the clip feeder 115. The outer wrap tongue 142 is shown deflected downward beneath the jaws 152.

Figure 14:
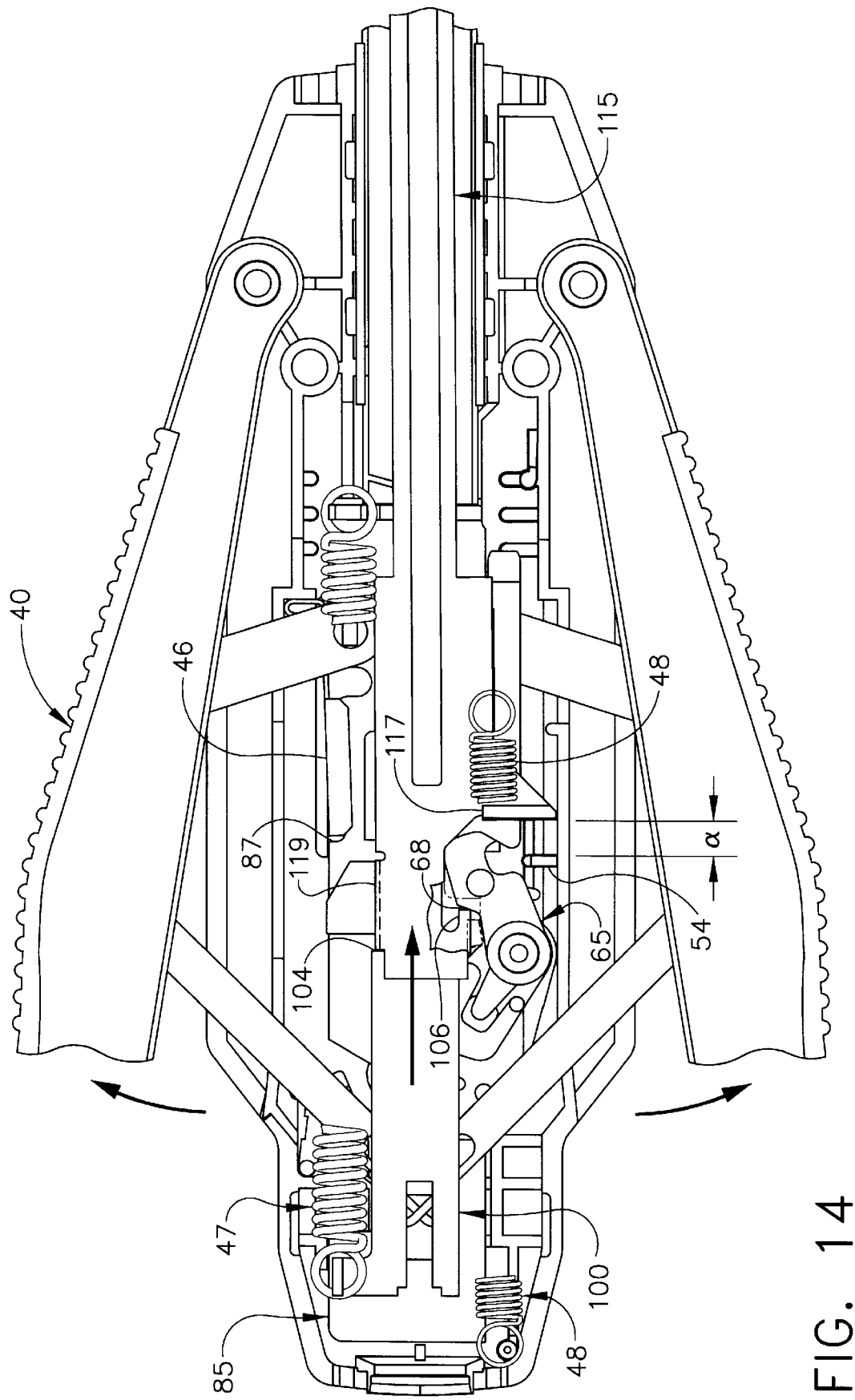
FIG. 14 is similar to the top view of FIG. 12 wherein the ring handles are in a first partially opened position.
Figure 15:
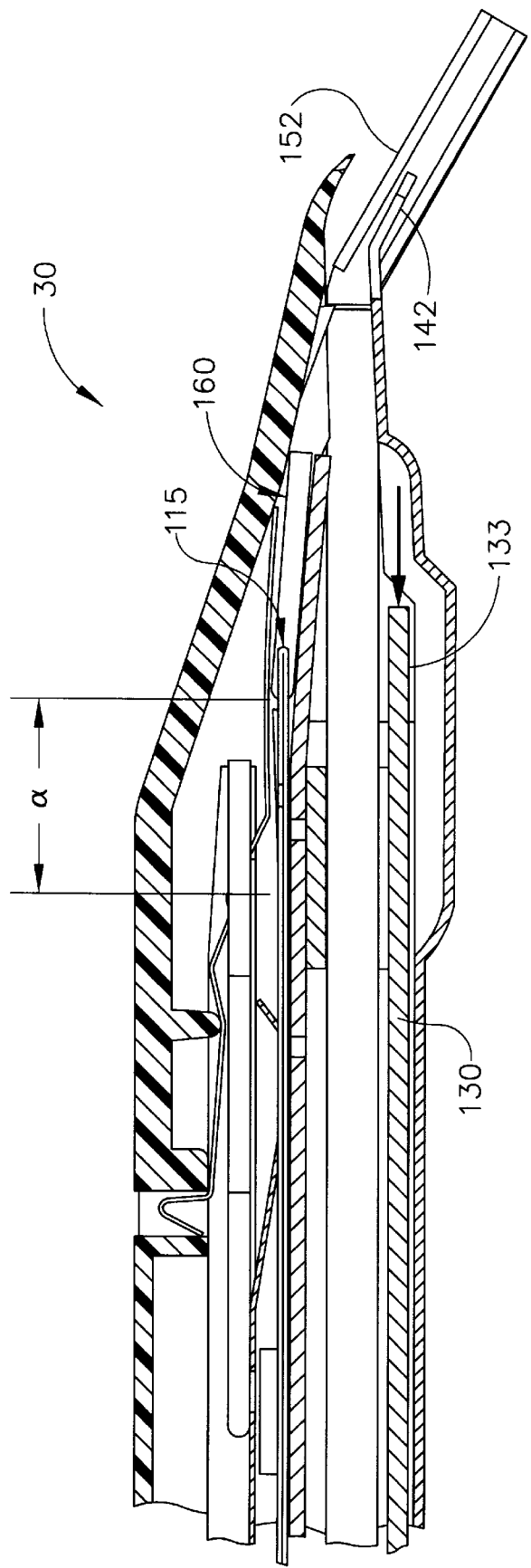
FIG. 15 is similar to that of FIG. 10, but with the jaws in a first partially opened position and the end effector components repositioned by the outward movement of the ring handles as shown in FIG. 14.

In FIGS. 14 and 15, the ring handles 40 of the preferred invention are moved from a closed position to a first open position to partially open the jaws 152, operatively couple the feeding mechanism 100, 115, and move the feeding mechanism 100, 115 and clip 160 distally an amount $\alpha$. Turning now to FIG. 14, the outward motion of the ring handles 40 (curved arrows) has moved the feed plate 100 distally in the direction indicated by the straight arrow and the forming plate 85 proximally in opposite directions relative to each other. This motion has reduced the length of the firing spring 47.

The feed plate 100 and the clip pusher 115 of the feeding mechanism 100, 115 are shown operatively coupled. The feed plate 100 has moved distally an amount $\epsilon$ (FIG. 12) to operatively couple with the clip pusher 115. The clip pusher 115 and feed plate 100 are operatively coupled by the contact of the proximal edge of the locking tab 119 with the proximal edge of the locking notch 104. The coupled feed plate 100 and clip pusher 115 are moved distally an additional amount $\alpha$ by the opening handles until the distal movement of the feeding mechanism 100, 115 is stopped by the contact of the trigger tab 106 of the feed plate 100 with the trigger notch 68 of the stationary trigger 65 (FIG. 14). This contact prevents further distal movement of the feeding mechanism 100, 115 and the clip 160 until the trigger mechanism 65, 75 is free to rotate clockwise. The feeding mechanism 100, 115 is biased distally against the trigger notch 68 by the elongated return spring 48 and is poised to place a clip 160 into the jaws.

The trigger mechanism 65, 75 of the present invention has a trigger tab 66 (FIG. 2) that extends downward from the trigger 65 and engages a trigger wall 90 (FIG. 2) extending from the feed plate 85. This engagement blocks the rotation of the trigger mechanism 65, 75 until the forming system 85, 130 opens the jaws 152 at which point the trigger tab 66 rotates out of the path of the trigger wall 90.

FIG. 15 shows a cross section of the distal end of the instrument wherein the clip pusher 115 has moved distally an amount α. This movement moves the clip 160, located between the bifurcated end of the clip pusher 115, distally from a first staged position to a second staged position. This staging process places the clip at an improved angle for insertion into the jaws 152.

Figure 16:
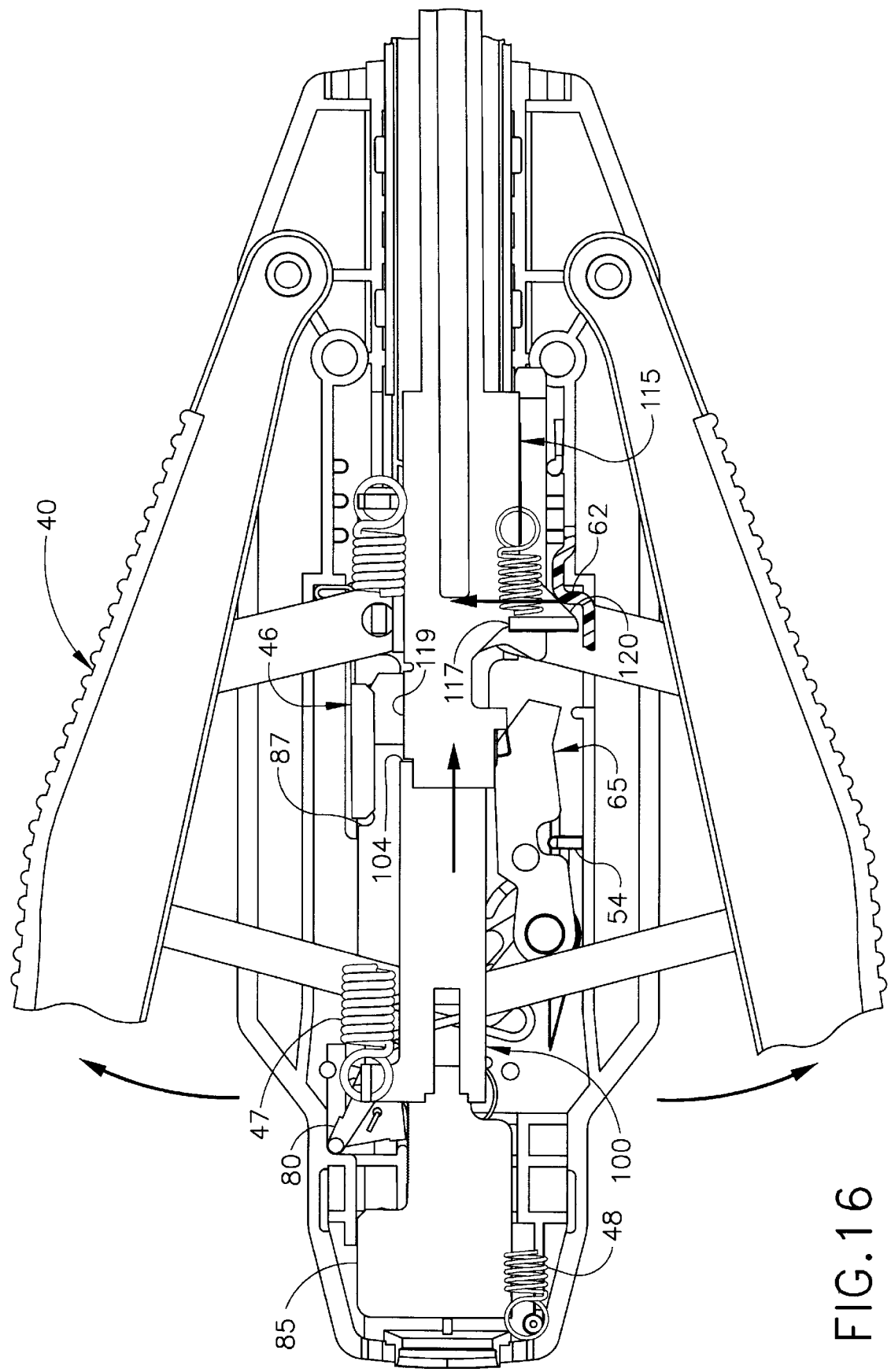
FIG. 16 is similar to the top view of FIG. 14 wherein the ring handles are moved outwardly to the fully opened position to fully open the jaws and to actuate the clip feeding mechanism.
Figure 17:
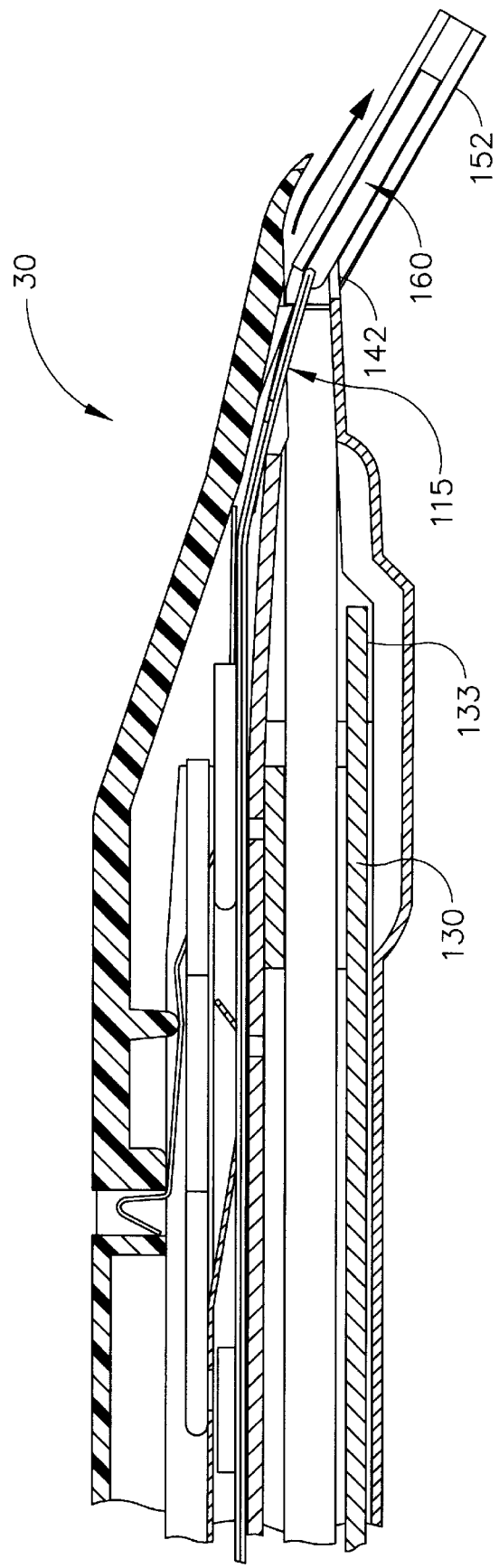
FIG. 17 is similar to that of FIG. 15, but with the jaws in a fully opened position and a clip being fed into the opened jaws.

Turning now to FIGS. 16 and 17, the ring handles 40 are shown in a second partially open position wherein they are moving outwards from the first partially open position of FIG. 14. The forming plate 85 has moved to the proximal most position to fully open the jaws 152 and has released the trigger mechanism 65, 75. The trigger mechanism 65, 75 has rotated clockwise and has released the feeding system 100, 115 and toggled the anti-backup mechanism 80, 86 into engagement. The feeding system 100, 115 is moving distally and is shown at a near distalmost position, e.g. just prior to the full placement of a clip 160 within the jaws 152. The firing spring 47 has provided the bias to move the forming plate 85 to the proximal most position, the feeding system 100, 115 distally, and the ring handles 40 generally open.

The feeding mechanism 100, 115 is shown operatively coupled and moving distally under the bias of the firing spring 47. The firing spring 47 will continue to bias the feed plate 100 distally, the former plate 85 proximally, and the ring handles 40 fully open. The clip pusher 115 has an angled pusher ramp 120 that is just contacting a pusher reset surface 62 (cross hatched section) formed in the cover 60. This contact biases the proximal end of the moving clip feeder 115 upwards in the direction of the vertical arrow and is shown just prior to decoupling the clip pusher 115 from the feed plate 100.

Turning now to the distal end of the instrument in FIG. 17, the clip pusher 115 is shown pushing the clip 160 into the jaws 152 (see arrow). The cam tongue 133 has moved distally to release the outer wrap tongue 142 which is in the process of deflecting back in between the fully open jaws 152.

Once the clip 160 is fully placed into the jaws 152 as shown in FIG. 18, the clip pusher 115 is decoupled from the feed plate 100. This decoupling is caused by the vertical bias applied to the proximal end of the clip pusher 115 (FIG. 16) by the contact of the angled pusher ramp 120 with the pusher reset surface 62 (as described above). The bias moves the locking tab 119 (FIG. 16) out of the locking notch 104 to decouple the clip pusher 115 from the feed plate 100. The reader is referred to FIG. 16 which shows the feeding mechanism 100, 115 just prior to decoupling. The return spring 48 will rapidly bias the decoupled clip pusher 115 to the proximal most position. Turning now to FIG. 18, this distal motion of the clip pusher 115 moves the distal end of the clip pusher 115 from a position adjacent to the clip 160, placed within the jaws, to a proximal position behind the distal-most clip of the plurality of clips within the shaft. As the ring handles 40 continue their outward movement, the feeding mechanism 100, 115 and the forming mechanism 85, 130 return to the configuration of FIGS. 3, 4, and 5 wherein the instrument of the present invention is ready to place another clip.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A multiple clip applier comprising:
   a handle portion;
   a pair of handles pivotally connected to said handle portion;
   a shaft extending from said handle portion, said shaft having a plurality of clips located therein;
   a pair of opposed, moveable jaws attached to and extending from said shaft, said jaws for receiving each of said clips serially therein when said jaws are in an open position, and for forming each of said clips received serially therein when said jaws are moved to a closed position;
   a moveable forming mechanism operatively connected to said handles, said forming mechanism moving said jaws:
   i) from the open position to the closed position as said handles are closed so as to form each of said clips received serially therein, and
   ii) from the closed position to the open position as said handles are opened so as to receive each of said clips serially therein; and
   a feeding mechanism operatively connected to said handles, said feeding mechanism having a feed plate moveable in response to opening and closing said handles, said feed plate releasably coupled to a clip pusher of said feed mechanism, wherein said clip pusher is stationary and uncoupled from said feed plate as said handles are closed, and said clip pusher is moveable and operatively coupled to said feed plate as said handles are opened so as to move each of said clips serially from said shaft into said jaws.

2. The applier of claim 1 wherein said feed plate and said forming mechanism move in opposite directions relative to each other as said handles are opened.

3. The applier of claim 2 wherein said clip pusher has proximal and distal ends, said feeding mechanism has an axis of motion, and the proximal end of said clip pusher moves laterally to the axis of motion of said feeding mechanism so as to operatively couple said clip pusher with said feed plate for the movement of each of said clips serially from said shaft into said jaws.

4. The applier of claim 3 wherein said clip pusher is operatively coupled at an angle (θ) with respect to said feed plate.

5. The applier of claim 4 wherein said clip pusher is uncoupled from said feed plate after each of said clips is moved serially from said shaft into said jaws by said clip pusher.

6. The applier of claim 5 wherein said clip pusher has a pusher ramp adjacent to the proximal end thereof, and said handle portion has a pusher reset feature thereon, said clip pusher reset feature laterally biasing said clip pusher ramp of said clip pusher so as to uncouple said clip pusher from said feed plate after each of said clips is moved serially from said shaft into said jaws by said clip pusher.

7. The applier of claim 6 wherein said clip pusher and said handle portion are coupled by a return spring, and when said clip pusher is uncoupled from said feed plate, and said handles are opened, the distal end of said clip pusher is biased proximally by said return spring, and the distal end of said clip pusher is moved from a distal position adjacent said clip placed within said jaws to a proximal position behind a distal-most clip of the plurality of said clips remaining within said shaft.

* * * * *